(12) United States Patent
Bieser et al.

(10) Patent No.: US 8,835,662 B2
(45) Date of Patent: Sep. 16, 2014

(54) CONTINUOUS PROCESS OF OXIDATIVE CLEAVAGE OF VEGETABLE OILS

(75) Inventors: Arno Bieser, Novara (IT); Giampietro Borsotti, Novara (IT); Francesca Digioia, Novara (IT); Adriano Ferrari, Novara (IT); Alessandro Pirocco, Novara (IT)

(73) Assignee: Novamont S.p.A., Novara (IT)

( * ) Notice: Subject to any disclaimer, the term of this patent is extended or adjusted under 35 U.S.C. 154(b) by 239 days.

(21) Appl. No.: 13/520,020

(22) PCT Filed: Dec. 29, 2010

(86) PCT No.: PCT/EP2010/070843
§ 371 (c)(1),
(2), (4) Date: Jun. 29, 2012

(87) PCT Pub. No.: WO2011/080296
PCT Pub. Date: Jul. 7, 2011

(65) Prior Publication Data
US 2012/0323028 A1 Dec. 20, 2012

(30) Foreign Application Priority Data
Dec. 30, 2009 (IT) .......................... MI2009A002360

(51) Int. Cl.
*C07C 51/16* (2006.01)
*C07C 51/09* (2006.01)
*C07C 51/245* (2006.01)

(52) U.S. Cl.
CPC ................. *C07C 51/09* (2013.01); *C07C 51/16* (2013.01); *C07C 51/245* (2013.01)

USPC ........... 554/132; 554/135; 554/136; 554/137; 554/138; 554/160

(58) Field of Classification Search
CPC ............ C11C 3/06; C11C 1/04; C07C 53/126
See application file for complete search history.

(56) References Cited

U.S. PATENT DOCUMENTS
4,606,863 A 8/1986 Nakazawa et al.

FOREIGN PATENT DOCUMENTS
WO WO-94/10122 A1 5/1994
WO WO-2007/039481 A1 4/2007
WO WO-2008/138892 A1 11/2008

*Primary Examiner* — Yate K Cutliff
(74) *Attorney, Agent, or Firm* — Novak Druce Connolly Bove + Quigg LLP

(57) ABSTRACT

There is described a continuous process for the oxidative cleavage of vegetable oils containing triglycerides of unsaturated carboxylic acids, for the obtainment of saturated carboxylic acids, comprising the steps of:
a) feeding to a first continuous reactor at least a vegetable oil, an oxidizing compound and a catalyst capable of catalyzing the oxidation reaction of the olefinic double bond to obtain an intermediate compound containing vicinal diols, and of
b) feeding to a second continuous reactor said intermediate compound, a compound containing oxygen and a catalyst capable of catalyzing the oxidation reaction of the vicinal diols to carboxylic groups, to obtain saturated monocarboxylic acids (i) and triglycerides containing saturated carboxylic acids with more than one acid function (ii);
c) separating the saturated monocarboxylic acids (i) from the triglycerides having more than one acid function (ii).
d) hydrolyzing in a third reactor the triglycerides having more than one acid function (ii) to obtain glycerol and saturated carboxylic acids with more than one acid function.

20 Claims, 4 Drawing Sheets

Hydrogen peroxide concentration in the reaction mixture during step a) of the Example 1 (continuous process according to the invention with a $H_2O_2$ starting concentration of 60%);

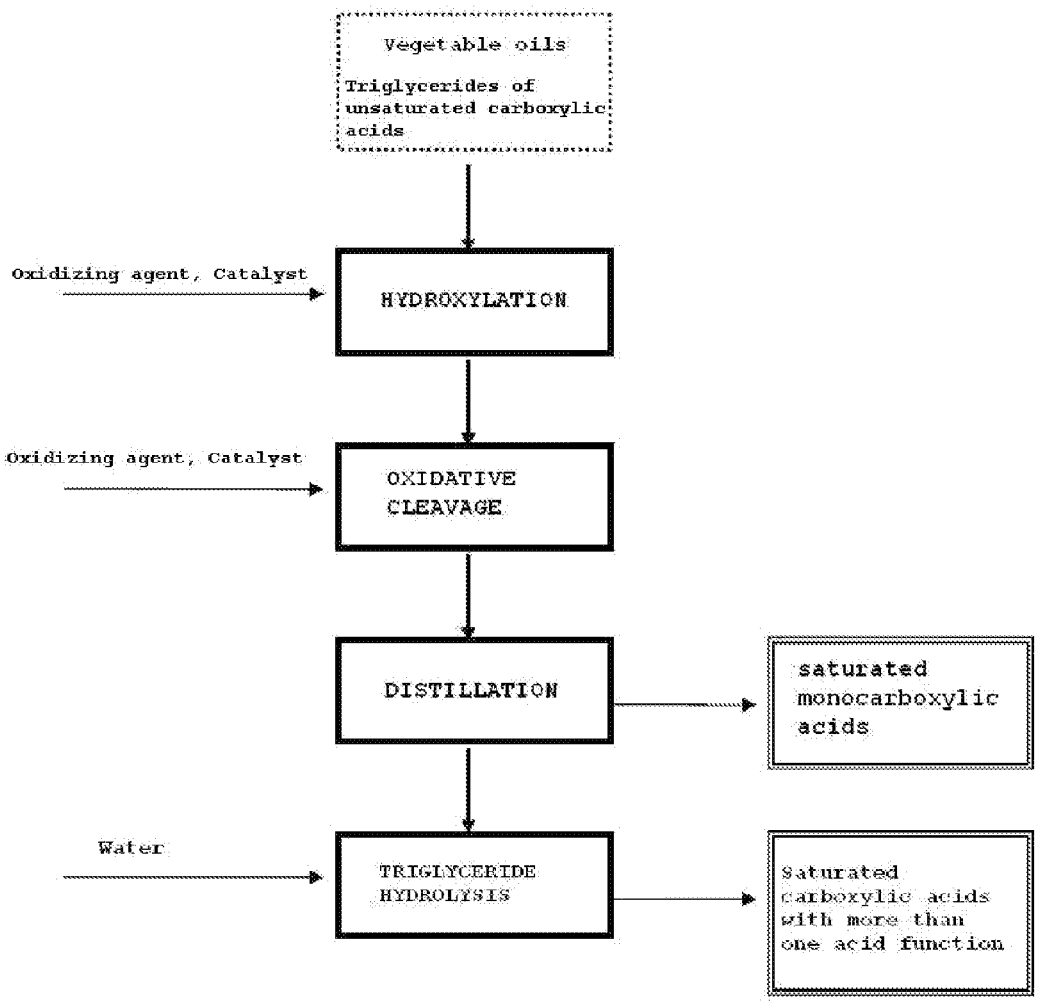
FIG. 1: The flow diagram of the process according to the invention

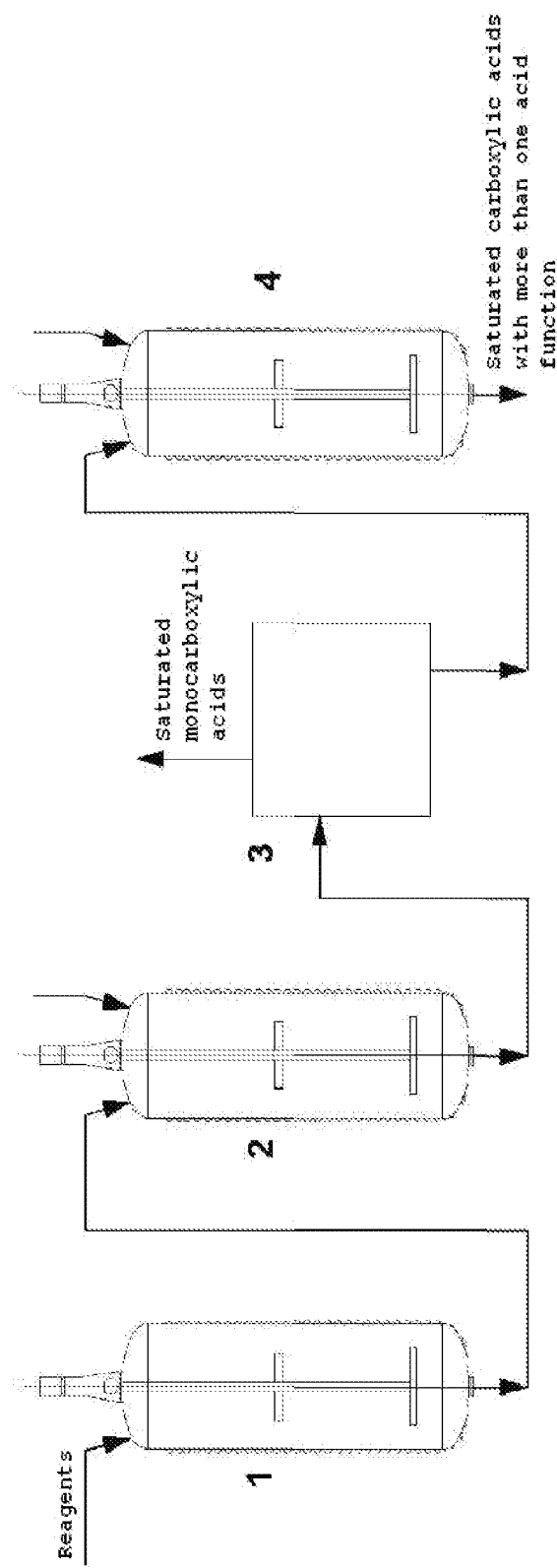
FIG. 2: A diagram of the plant in which the process takes place

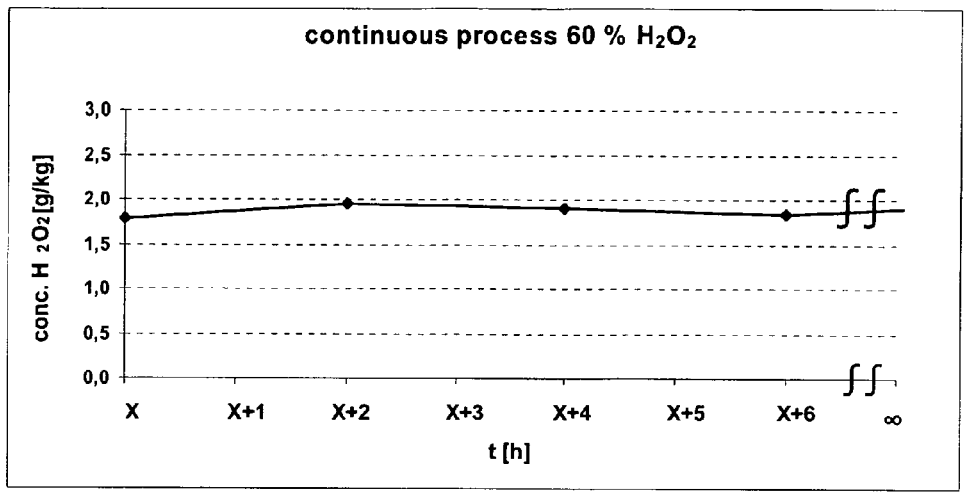
FIG. 3: Hydrogen peroxide concentration in the reaction mixture during step a) of the Example 1 (continuous process according to the invention with a $H_2O_2$ starting concentration of 60%);
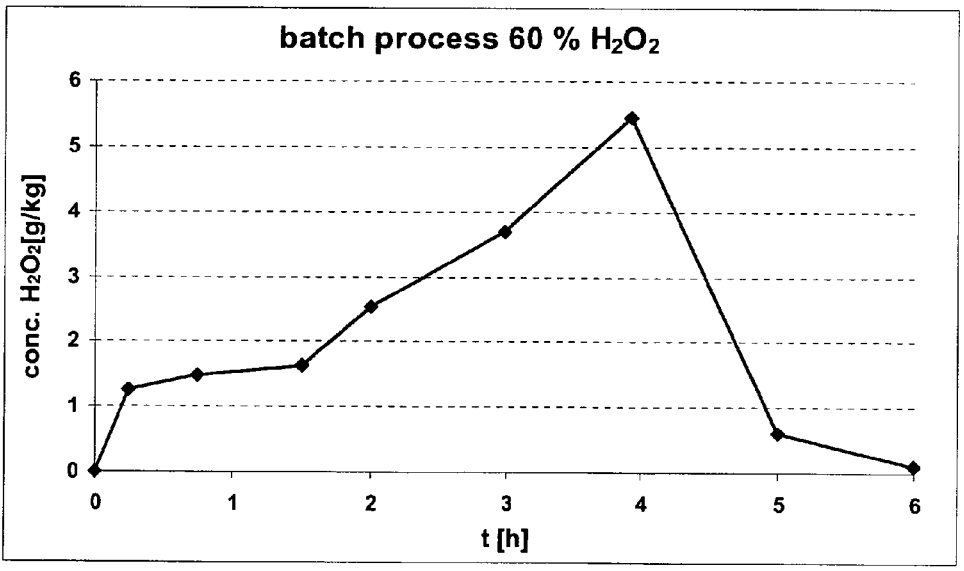
FIG. 4: the time-course concentration of hydrogen peroxide during step a) of Example 2 Comparative (batch process with a $H_2O_2$ starting concentration of 60%).

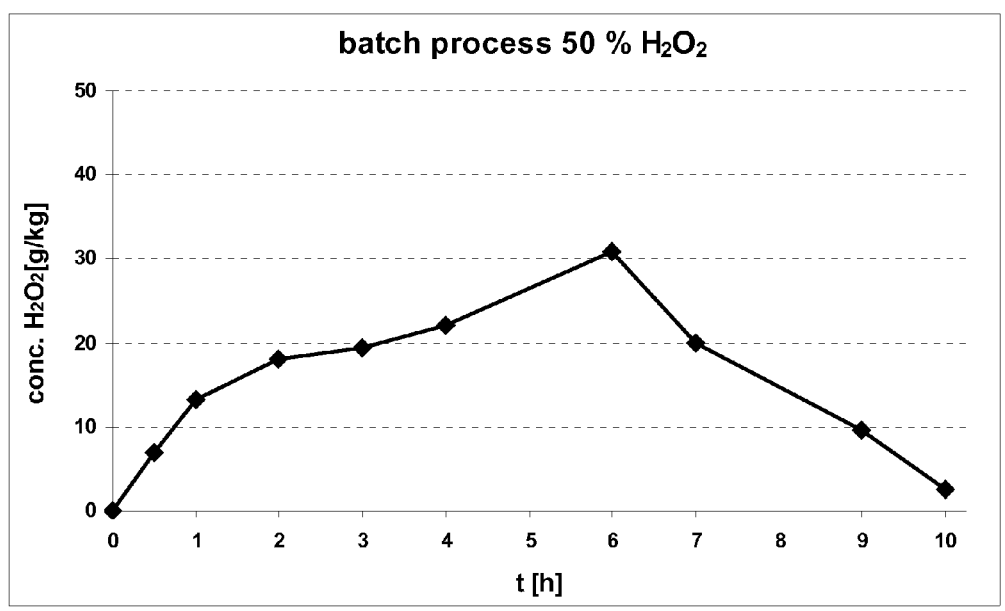
FIG. 5: the time-course concentration of hydrogen peroxide during step a) of Example 3 Comparative (batch process with a $H_2O_2$ starting concentration of 50%).

CONTINUOUS PROCESS OF OXIDATIVE CLEAVAGE OF VEGETABLE OILS

CROSS REFERENCE TO RELATED APPLICATIONS

This application is a National Phase filing under 35 U.S.C. §371 of PCT/EP2010/070843 filed on Dec. 29, 2010; and this application claims priority to Application No. MI2009A002360 filed in Italy on Dec. 30, 2009 under 35 U.S.C. §119; the entire contents of all are hereby incorporated by reference.

The present invention relates to a continuous process for the oxidative cleavage of vegetable oils containing triglycerides of unsaturated carboxylic acids, for the obtainment of saturated carboxylic acids, comprising the steps of:
a) feeding to a first reactor at least a vegetable oil, an oxidizing compound and a catalyst capable of catalyzing the oxidation reaction of the olefinic double bond to obtain an intermediate compound containing vicinal diols, and of
b) feeding to a second reactor said intermediate compound, a compound containing oxygen and a catalyst capable of catalyzing the oxidation reaction of the vicinal diols to carboxylic groups, to obtain saturated monocarboxylic acids (i) and triglycerides containing saturated carboxylic acids with more than one acid function (ii);
c) separating the saturated monocarboxylic acids (i) from the triglycerides having more than one acid function (ii).
d) hydrolyzing in a third reactor the triglycerides having more than one acid function (ii) to obtain glycerol and saturated carboxylic acids with more than one acid function.

Processes for the oxidative cleavage of vegetable oils containing triglycerides of unsaturated carboxylic acids are known in the literature.

For example, the patent application WO2008/138892 describes a batch process for the oxidative cleavage of vegetable oils characterized in that the oxidation reactions are performed on non-modified oils, without the addition of organic solvents and in the presence of limited quantities of water (water:diol<1:1).

The oxidation reactions described are significantly exothermic and require constant control, together with adequate removal of the heat developed in order to prevent an excessive increase of the temperature.

The oxidation phase of the unsaturated carbons to form vicinal diols, in particular, is subject to the risk of explosive decomposition of the peroxide used as oxidizing agent, as peroxide is very unstable in conditions of high temperature.

Moreover, a further limit of the entire process is related to the accidental accumulation of oxidizing agent, which can cause sudden acceleration of the reaction with consequent uncontrolled increase of the temperature. Such accumulation can depend on a low reaction velocity or on difficulty in the mixing of oxidizing agents with reagents.

In the oxidative cleavage step of the vicinal diols, for example, significant difficulties are encountered in mixing, as at the conditions used the reagents form a liquid phase characterized by high viscosity, while the oxidizing agent is in gaseous phase.

Furthermore, the mechanism of the oxidative cleavage reaction of the vicinal diols with oxygen has been demonstrated to be of radical type. Such type of reaction shows an induction time in which the appropriate radicals concentration has to be reached before starting the reaction; after this time the reaction starts propagating exponentially and uncontrolled, with the formation of by-products having, different chain length due to lack of selectivity.

To overcome the aforesaid drawbacks, the present continuous process for the production of carboxylic acids starting from vegetable oils has been developed. In said process, each of the oxidation reactions is conducted continuously and not in a batch process.

The term continuous is intended as a process in which the operations to feed reagents and to remove products take place simultaneously for the entire duration thereof and in which, in each step, the process conditions (i.e. temperature, pressure, flow rate, etc.) remain substantially unchanged.

The continuous process according to the present invention is more effectively controllable with respect to known processes, making it possible to feed high concentrations of oxidizing agent in safe conditions during step a) of the process.

Moreover, the continuous process according to the invention solves the difficulties of mixing the oxidizing agent during the oxidative cleavage reaction of the diols, linked to the high viscosity of the reaction mixture. In fact, in said process for the entire duration of step b) the reaction mixture contains a high percentage of reaction products which, being more fluid than the reagents, contribute towards significantly decreasing the viscosity of the system.

In the continuous process according to the invention it is also possible to maintain constant and low the radicals concentration during step b), thus limiting the formation of by-products and increasing the reaction yield.

BRIEF DESCRIPTION OF THE DRAWINGS

The process according to the invention will now be described in greater detail with reference to the FIGS. 1-5, wherein:

FIG. 1 is a flow diagram of the process according to the invention;

FIG. 2 is a diagram of the plant in which the process takes place;

FIG. 3 is a diagram showing the hydrogen peroxide concentration in the reaction mixture during step a) of Example 1 (continuous process according to the invention with a $H_2O_2$ starting concentration of 60%);

FIG. 4 is a diagram showing the time-course concentration of hydrogen peroxide during step a) of Example 2 Comparative (batch process with a $H_2O_2$ starting concentration of 60%); and FIG. 5 is a diagram showing the time-course concentration of hydrogen peroxide during step a) of Example 3 Comparative (batch process with a $H_2O_2$ starting concentration of 50%.

The present invention relates in particular to a continuous process for the oxidative cleavage of vegetable oils containing triglycerides of unsaturated carboxylic acids, for the obtainment of saturated carboxylic acids, comprising the steps of:
a) feeding to a first continuous reactor (1) at least a vegetable oil and an oxidizing compound in the presence of a catalyst capable of catalyzing the oxidation reaction of the olefinic double bond to obtain an intermediate compound containing vicinal diols; and of
b) feeding to a second continuous reactor (2) said intermediate compound, oxygen or a compound containing oxygen, and a catalyst capable of catalyzing the oxidation reaction of the diols to carboxylic groups, to obtain saturated monocarboxylic acids (i) and triglycerides containing saturated monocarboxylic acids with more than one acid function (ii);

c) transferring the product of step b) to an apparatus (3) suitable to separate the saturated monocarboxylic acids (i) from the triglycerides having more than one acid function (ii);

d) hydrolyzing in a third reactor (4) said triglycerides (ii) to obtain glycerol and saturated carboxylic acids with more than one acid function.

The starting material for the process according to the present invention is a vegetable oil, or a mixture of vegetable oils, containing triglycerides of unsaturated carboxylic acids. These vegetable oils are intended both as non-modified pressed products and as an oil that has been subjected to chemical or chemical-physical modifications, such as purification treatments or enzymatic enrichment operations. Examples of vegetable oils are: soybean oil, olive oil, castor oil, sunflower oil, peanut oil, maize oil, palm oil, jatropha oil, cuphea oil, oils from Brassicaceae such as *Crambe abyssinica, Brassica carinata, Brassica napus* (rapeseed), Lesquerella, and other oils with a high monounsaturated acid content. The use of sunflower seed oil and oils from Brassicaceae is particularly preferred. The use of sunflower oil with a high oleic content and oils from Brassicaceae with a high erucic content is even more preferred.

The triglycerides can contain both monounsaturated and polyunsaturated carboxylic acids. Examples of unsaturated carboxylic acids are: 9-tetradecenoic acid (myristoleic acid), 9-hexadecenoic acid (palmitoleic acid), 9-octadecenoic acid (oleic acid), 12-hydroxy-9-octadecenoic acid (ricinoleic acid), 9-eicosenoic acid (gadoleic acid), 13-docosenoic acid (erucic acid), 15-tetracosenoic acid (nervonic acid), 9,12-octadecadienoic acid (linoleic acid), and 9,12,15-octadecatrienoic acid (linolenic acid).

Monounsaturated carboxylic acids are particularly preferred. The use of oleic acid and of erucic acid is particularly advantageous in the process according to the invention. In these cases pelargonic acid with high yields is obtained as saturated monocarboxylic acid.

In the process according to the invention the reactors 1 and 2 used to perform steps a) and b), are continuous reactors preferably connected each other by means a gear pump. The use of these continuous reactors allows a reduction of the reaction volumes, facilitating heat exchange.

In a preferred embodiment of the process, the reactors 1 and 2 are of the CSTR (Continuous Stirred-Tank Reactor) type. Each of the CSTRs 1 and 2 can advantageously be substituted by several reactors of the same type arranged in series, determining an increase in the surface/volume ratio (consequently further facilitating the heat exchange during the reaction) and the reduction of the total reaction volume.

In step b) continuous reactors of gas/liquid type are advantageously used. Preferably, jet loop reactors (CSTR Loop), which promote, contact between the oxidizing agent in gaseous phase and the reaction mixture in liquid phase, are used.

Both steps a) and b) are preferably conducted without the addition of organic solvents The intermediate product obtained as output from the reactor (1) is continuously fed, preferably by a gear pump, to the reactor (2), where it is allowed to react with oxygen or a compound containing oxygen without requiring any preliminary purification treatment.

In a preferred embodiment of the process according to the invention at the end of step a) the catalyst is not removed.

In a preferred embodiment of the process, step b) is conducted without the addition of water besides that in which the catalyst is dissolved. Advantageously, throughout the duration of said step b) the aqueous phase/organic phase weight ratio is maintained below 1:3.

The oxidizing substance used to perform step a) of the process according to the invention is preferably selected from osmium tetroxide, permanganates, hydrogen peroxide, alkyl hydroperoxides and percarboxylic acids as, for example, performic acid, peracetic acid or perbenzoic acids. Said oxidizing substance is more preferably an aqueous solution of hydrogen peroxide in concentrations between 30 and 80% (w/w), preferably between 40 and 70% and even more preferably between 49 and 65%.

In the continuous process according to the present invention it is possible to use solutions of hydrogen peroxide even at very high concentrations. In fact, the continuous nature of the process allows the concentration of peroxide to be kept constant during the reaction, preventing dangerous phenomena of accumulation thereof which can instead occur during batch type reactions. Surprisingly, the applicant has found that the $H_2O_2$ concentration during the continuous process according to the invention is even lower than the one observed during a batch process performed with lower starting concentration of hydrogen peroxide.

The use of hydrogen peroxide solutions at high concentrations has the advantage of introducing lower quantities of dilution water into the reaction mixture.

The diol resulting from step a) and coming out from reactor 1 is fed to reactor 2, where it is made to react—in step b)—with oxygen or with a compound containing oxygen. The use of air is particularly advantageous. Oxygen enriched air can also be used.

The catalyst of step a) belongs to the group of transition elements. Advantageously, Fe, Mn, Mo, Nb, Os, Re, Ti, V, W, Zr and their acids, alkaline salts and complexes are used as catalysts in homogeneous or heterogeneous phase, optionally in a supported or nanostructured form. The use of tungstic acid or phosphotungstic acid is particularly preferred. Said catalyst is present in quantities between 0.03% and 3% by moles, preferably between 0.05% and 1.8% by moles and even, more preferably between 0.06% and 1.5% by moles with respect to the total moles of unsaturations. In a preferred embodiment of the process, the catalyst can be fed in solution form in a non-organic solvent.

With regard to the catalyst of step b), it belongs to the group of the transition elements. Advantageously, Ce, Cr, Co, Cu, Mn, Mo, Re, Os, V and W and their acids, alkaline salts and complexes are used as catalysts in homogeneous or heterogeneous phase, optionally in a supported or nanostructured form. The use of cobalt salts such as acetate, chloride, sulphate, bromide and nitrate, used in quantities between 0.05% and 3% by moles, preferably between 0.1% and 2% by moles and even more preferably between 0.3% and 1.5% by moles with respect to the diol produced in step a) is particularly preferred. The use of cobalt acetate and cobalt chloride is particularly preferred.

An inorganic acid can be added to the catalyst of step b). Examples of inorganic acid are phosphoric acid, sulphuric acid, hydrochloric acid, perchloric acid and mixtures thereof. The startup phase of the continuous process according to the invention can be carried out by adding a small quantity of the intermediate compound obtained with step a), as the diols contained therein promote activation of the reaction. Said intermediate compound can be added in a quantity ≤5%, preferably ≤3% in weight with respect to the starting oil. Advantageously, during step a) of the process according to the invention, nitrogen or air are made to flow to remove a part of the water produced in the process. In this manner excessive dilution of $H_2O_2$ of is avoided. An alternative to the flow of these gases is vacuum evaporation.

The reaction temperature of step a) and of step b) of the present process is advantageously between 45 and 95° C., preferably between 50 and 90° C.

The reaction temperature of step a) is advantageously between 55 and 80° C.

The reaction temperature of step b) is advantageously between 55 and 90° C. and even more advantageously between 60 and 70° C.

Advantageously, to perform both step a) and step b) of the present process, the average retention time in the reactor is between 2 and 8 hours.

In a preferred embodiment of the process, the intermediate product obtained from step a) is fed directly to the reactor in which step b) is performed. In fact, it has surprisingly been found that by feeding the intermediate product directly to the oxidative cleavage reactor, this reaction time is decreased with respect to batch reaction, due to the greater reactivity of this intermediate product. This increase in reactivity also determines a significant increase in the reaction yield.

The process according to the invention can be advantageously performed at atmospheric pressure or in any case at moderate partial oxygen pressures therefore resulting particularly advantageous in terms of industrial production.

Step a) is preferably performed at atmospheric pressure or under a slight vacuum.

Step b) is preferably performed with air at a pressure of $\leq 50*10^5$ Pa, preferably $\leq 25*10^5$ Pa. Advantageously, the aqueous phase of the product obtained as output from step b) is separated from the organic phase.

Organic phase separation can be advantageously performed by continuous centrifuging by means of a disc separator or with other established separation techniques.

Optionally a small amount of organic solvent can be added to improve the separation of the two phases.

The aqueous phase contains the catalysts of steps a) and b) which can be recovered and optionally recycled as catalysts of step b). The organic phase is a clear oil consisting of a mixture substantially comprising saturated monocarboxylic acids and triglycerides containing saturated carboxylic acids having more than one acid function, saturated monocarboxylic acids present in the starting mixture and vicinal diol formed during step a).

In a preferred embodiment of the process, in which oil with high oleic content is used as starting material, the organic phase is substantially composed of pelargonic acid and triglycerides of azelaic, palmitic, stearic and dihydroxystearic acid.

In another preferred embodiment of the process, in which oils with high erucic content are used as starting material, the organic phase is substantially composed of pelargonic acid and triglycerides of azelaic, brassylic, palmitic, stearic, dihydroxystearic and dihydroxybehenic acid.

In step c) of the process according to the invention, the organic phase obtained as oxidative cleavage product is fed to an apparatus (3) suitable to separate the saturated monocarboxylic acids from the triglycerides containing saturated carboxylic acids having more than one carboxylic function. Separation is advantageously performed by distillation processes.

Distillation processes not subjecting the mixture obtained in step b) to high thermal stress, such as distillation in vapor current, thin film distillation, falling film distillation, molecular distillation, are preferred. Advantageously, the mixture of evaporated monocarboxylic acids can be subjected to further fractioned distillation to obtain monocarboxylic acids with a greater degree of purity.

In a preferred embodiment of the process, the monocarboxylic acids are separated from the triglycerides by distillation using thin film evaporators.

The triglycerides containing saturated carboxylic acids having more than one acid function present in the residual organic phase are in turn hydrolyzed to form glycerol and saturated carboxylic acids in step d) of the process (reactor 4). The hydrolysis reaction can be performed using different techniques, such as only with water, with strong acid ion exchange resins or by catalyzing the reaction with enzymes.

In the case of hydrolysis with water, the reaction takes place at temperatures between 150 and 350° C., preferable between 180 and 320° C., at the corresponding vapor equilibrium pressure, with or without the addition of a catalyst and with a water/oil ratio preferably comprised between 0.5:1 and 5:1.

Hydrolysis with strong acid ion exchange resins is performed at the temperature of 100-140° C. Examples of suitable resins are those of the Amberlyst® and Amberlite® type (both produced by Rohm and Haas Co.).

In the case of reaction catalyzed by enzymes (lipases), it is advantageous to use lipases selected within the group comprising: *Candida cylindracea, Candida antarctica, Pseudomonas* sp., porcine pancreatic lipases, *Candida rugosa, Geotrichum candidum, Aspergillus niger, Mucor miehei, Rhizopus arrhizus, Rhizopus delemar, Rhizopus niveus, Chromobacterium viscosum, Thermomyces lanuginosus, Penicillium cyclopium*.

In a preferred embodiment of the process according to the invention, the hydrolysis reaction is performed in continuous by using only water at 260-300° C., in a plug flow tubular reactor, with a reaction time preferably comprised between 1 minute and 1 hour, preferably between 3 minutes and 30 minutes. The aqueous phase/organic phase ratio is comprised between 1:1 and 3:1.

Following hydrolysis, an organic phase and an aqueous phase containing glycerol are obtained. Advantageously, the aqueous phase is separated and concentrated to recover the glycerol by using well established separation techniques.

The organic phase principally contains saturated carboxylic acids with more than one acid function. Monocarboxylic acids, released following the hydrolysis reaction, diol and a reaction residue consisting of oligomers are also contained in the organic phase.

The carboxylic acids are advantageously separated from diol and residue by distillation in a thin film evaporator or by means of molecular distillation.

The diol and the residue thus separated can be used, for example, as biofuel or recycled in, the oxidative cleavage reactor 2 (step b).

The evaporated carboxylic acids are then advantageously subjected to column distillation to separate the monocarboxylic acids with low molecular weight, thus purifying the saturated carboxylic acids having more than one acid function.

In a preferred embodiment of the process according to the invention, these carboxylic acids are further purified from the monocarboxylic acids with high molecular weight by means of extraction in water.

In a preferred embodiment of the process according to the invention, these carboxylic acids are further purified by fractioned crystallization by means of wash column (melt crystallization)

According to the type of vegetable oils used as starting material, different saturated carboxylic acids having more than one acid function can be obtained, such as: oxalic acid, malonic acid, succinic acid, glutaric acid, adipic acid, pimelic acid, suberic acid, azelaic acid, sebacic acid, undecandicarboxylic acid, dodecandicarboxylic acid, brassylic acid, tetradecandicarboxylic acid, pentadecandicarboxylic acid.

In a preferred embodiment of the process according to the invention, azelaic acid is principally obtained from the oxidative cleavage reaction of oils with high oleic content.

In another preferred embodiment of the process, brassylic acid is principally obtained from the oxidative cleavage reaction of oils with high erucic content.

The process according to the invention will now be described according to the following non-limiting examples and FIGS. 3-5.

The concentration (w/w) of hydrogen peroxide in the reaction mixture can be determined by techniques well-known in the art. The hydrogen peroxide concentration of Examples 1-3 is determined according to the method described in the patent application WO 02/063285.

EXAMPLE 1

Step a)

The following substances were fed continuously to a CSTR with a working capacity of 100 L, equipped with a stirrer and with an adequate temperature regulation system:
- sunflower oil with high oleic acid content (82% oleic, 10% linoleic, 3.5% stearic; flow rate 12.5 kg/h)
- aqueous solution of hydrogen peroxide at 60% (flow rate 2.9 kg/h);
- tungstic acid ($H_2WO_4$) (flow rate 38 g/h; 0.35% by moles with respect to the moles of unsaturations).

The reaction was, carried out at a constant temperature of 62° C., under vacuum (absolute pressure of $0.10$-$0.20*10^5$ Pa) to evaporate the water fed together with the hydrogen peroxide; the evaporated gas was collected and condensed (approximately 1.25 kg/h of water).

FIG. 3 shows the hydrogen peroxide over-all concentration during step a).

As can be seen in FIG. 3, the over-all hydrogen peroxide concentration in the reactor was constant at about 2 g/kg.

The intermediate product containing vicinal diols was continuously discharged from the reactor and fed to step b) by means of a gear pump, adjusted to maintain a constant level in the reactor, with a flow rate of approximately 14 kg/h.

Step b)

The step b) was performed in a jet loop reactor with a working capacity of 100 l equipped with a 4 $m^3$/h recirculation pump and heat exchanger. The intermediate product of step a) was continuously fed with a flow rate of 14 kg/h together with:
- cobalt acetate ($Co(CH_3COOH)_2 \cdot 4H_2O$) dissolved in an aqueous current (flow rate 4 kg/h) partly coming from recycling of the catalytic solution (approximately 2 kg/h);
- pressurized air ($20*10^5$ Pa; flow rate 13 to 16 kg/h).

The air flow rate was adjusted to maintain a constant $O_2$ content (approximately 10-12%) at the reactor outlet.

The reaction was conducted at 72° C. and at $20*10^5$ Pa pressure, keeping constant the reaction volume to 60 l.

The viscosity of the intermediate product of step a) at 72° C. was 300 cP. The viscosity of the reaction mixture during step b) was constant at approximately 35 cP.

The reaction started instantly; the reaction time was of about 3 h 30 min.

The reaction mixture of step b) was continuously discharged from the jet loop reactor and fed to a liquid/liquid centrifuge to separate the oily phase from the aqueous phase. Approximately 16 kg/h of oily product was obtained.

Step c)

The separated oily phase was dried and degassed, and then transferred to a thin film evaporator. The vapor phase produced in the evaporator essentially contained monocarboxylic acids and was fractioned inside a rectification column, in order to separate the pelargonic acid from the lighter monocarboxylic acids. The main component of the lighter monocarboxylic acids fraction (byproducts of the oxidative cleavage reaction) was octanoic acid.

Approximately 4.5 kg/h of vapor phase containing monocarboxylic acids (raw pelargonic acid), of which 4.2 kg/h was pelargonic acid with a titer of over 99%, was obtained. The 4.5 kg/h current of raw pelargonic acid contained approximately 0.13 kg/h of octanoic acid.

An organic current of approximately 10.3 kg/h, containing as major component triglycerides with more than one carboxylic function, was extracted from the bottom of the evaporator.

Step d)

The organic current was pumped at high pressure to a hydrolysis reactor of tubular plug flow type, where it was mixed with a current of preheated water. The overall flow rate of the water/oil mixture was approximately 33 kg/h.

The reactor operates at conditions of 300° C. and $105*10^5$ Pa with a reaction time of 20 min. The hydrolyzed reaction mixture was cooled to 2-5° C. A solid/liquid slurry was obtained, from which the aqueous phase containing glycerol was separated by a solid/liquid continuous filtration centrifuge.

After drying and degassing, the organic phase, rich in azelaic acid, was transferred to a thin film evaporator. A liquid current, of 2.8 kg/h, consisting of a mixture of saturated products, was extracted from the bottom of the evaporator.

The vapor phase was fed to a rectification column by which a current of 0.8 kg/h, consisting of a mixture of light monocarboxylic acids with a pelargonic acid content of approximately 70% in weight, was distilled. Approximately 6.6 kg/h of a mixture of dicarboxylic acids (principally azelaic acid) with a content of heavy monocarboxylic acids of 10% to 12% (essentially palmitic acid and stearic acid) was obtained from the bottom of the rectification column.

EXAMPLE 2

Comparative

Step a) Performed Batchwise Vs Continuous with 60% $H_2O_2$

A batch process was performed placing in a 100 l reactor the following substances:
- 80 kg of sunflower oil with high oleic content (composition as in Example 1),
- 400 g of tungstic acid (0.7% by moles with respect to the unsaturated fatty acid),
- 4 kg of raw hydroxylated oil (intermediate obtained at the end of step (a) coming from a previous reaction, the so-called reaction activator).

The temperature was raised to 60-65° C. and 18.5 l of 60% solution of $H_2O_2$ were added in 4 h.

During the reaction nitrogen was fluxed to distil a part of the water of the process and to prevent excessive dilution of $H_2O_2$.

Once the addition of $H_2O_2$ was completed, the reaction was continued at 65° C. for 2 h to obtain the intermediate product containing vicinal diols.

FIG. 4 shows the time-course concentration of hydrogen peroxide during step a) of Example 2 Comparative. As can be seen in FIG. 4, the hydrogen peroxide concentration in the reaction mixture strongly varied reaching a peak two times superior than in Example 1 (FIG. 3).

In the continuous process according to Example 1 (FIG. 3), the concentration of $H_2O_2$ remained constant and on a significantly lower level leading to a safer process.

EXAMPLE 3

Comparative $H_2O_2$ Concentration Effect in Step a) Performed Batchwise

The step a) of a batch process was performed according to Example 2 Comparative with the same total amount of $H_2O_2$ but with a lower starting concentration.

22.4 l of 50% $H_2O_2$ solution of were added in the reactor in 6 h.

Once the addition of $H_2O_2$ was completed, the reaction was continued at 65° C. for 4 h. Due to the lower starting concentration of hydrogen peroxide, a longer reaction time was required with respect to Example 2 Comparative.

FIG. 5 shows the time-course concentration of hydrogen peroxide during step a) of Example 3 Comparative. It can be noted that the hydrogen peroxide concentration was considerably higher than the $H_2O_2$ concentration in Example 1 (FIG. 3), notwithstanding the hydrogen peroxide starting concentration being lower.

EXAMPLE 4

Comparative

Step b) Performed Batchwise Vs Continuous

The mixture formed at the end of the reaction step (a) of Example 2 Comparative was discharged. 70 kg of this intermediate product were transferred to a jet loop reactor.

19 Kg of aqueous solution of 1% cobalt acetate were added (0.4% by moles with respect to the diol produced in step (a)). The reactor was brought to 72° C. and to a pressure of $22*10^5$ Pa with air to perform step (b). Air was continuously fluxed to provide a sufficient supply of oxygen. After an induction period of 1 h 30 min. the reaction began. The beginning of the reaction was highlighted by the increase in temperature of the mixture, due to the exothermia of the oxidative cleavage. The batch reaction lasted 5 h.

At the end of step (b) hot separation of the aqueous phase from the organic phase was performed. The organic phase was then distilled by steam distillation to separate 22.6 Kg of raw pelargonic acid containing pelargonic acid and short-chain free monocarboxylic acids (by-products of the oxidative cleavage reaction), of which approximately 2 kg were octanoic acid. The distillation residue (49.7 kg) consisted mainly of triglycerides of azelaic acid. The corresponding yield for the oxidative cleavage reaction (step b)) was of about 70% with respect to the moles theoretically obtainable.

The conversion achieved after 3 h 30 min. reaction of step b) in the continuous process according to Example 1 was higher than the final yield reached after 5 h reaction in the batch process (Example 4 Comparative), as can be seen in Table 1:

TABLE 1

| Oxidative cleavage reaction yields (% moles of theoretical amount) | Example 1 | Example 4 Comparative |
|---|---|---|
| Pelargonic acid | 79.2 | 69.9 |
| Azelaic acid | 80.1 | 72.8 |

The selectivity of the oxidative cleavage reaction in the in the continuous process according to Example 1 was also higher than in the batch process, as can be seen in Table 2, showing that the by-product/product ratio was lower.

TABLE 2

| By-product/product (% w/w) | Example 1 | Example 4 Comparative |
|---|---|---|
| Octanoic acid/raw Pelargonic acid | 2.9 | 8.8 |

The invention claimed is:

1. Continuous process for the oxidative cleavage of vegetable oils containing triglycerides of unsaturated carboxylic acids, for the obtainment of saturated carboxylic acids, characterized by comprising the steps of:
   a) feeding to a first continuous reactor at least a vegetable oil and an oxidizing compound in the presence of a catalyst capable of catalyzing the oxidation reaction of the olefinic double bond to obtain an intermediate compound containing vicinal diols;
   b) feeding to a second continuous reactor said intermediate compound, oxygen or a compound containing oxygen, and a catalyst capable of catalyzing the oxidation reaction of said diols to carboxylic groups, to obtain saturated monocarboxylic acids (i) and triglycerides containing saturated monocarboxylic acids with more than one acid function (ii);
   c) transferring the product of step b) to an apparatus suitable to separate the saturated monocarboxylic acids (i) from the triglycerides having more than one acid function (ii); and
   d) hydrolyzing in a third reactor said triglycerides (ii) to obtain glycerol and saturated carboxylic acids with more than one acid function;
   the operations to feed reagents and to remove products taking place simultaneously for the entire duration of the process and within each step the process conditions remain substantially unchanged.

2. Process according to claim 1, wherein the vegetable oils belong to the group of oils having a high content of monounsaturated acids such as soybean oil, olive oil, castor oil, sunflower oil, peanut oil, maize oil, palm oil, jatropha oil, cuphea oil, oils from Brassicaceae, and mixtures thereof 3. Process according to claim 2, wherein the oil having a high content of monounsaturated acids is sunflower oil, oil from Brassicaceae, and mixtures thereof 4. Process according to claim 2, wherein the unsaturated carboxylic acids of the triglycerides contained in the vegetable oil belong to the group consisting of 9-tetradecenoic acid (myristoleic acid), 9-hexadecenoic acid (palmitoleic acid), 9-octadeceneoic acid (oleic acid), 12-hydroxy-9-octadeceneoic acid (ricinoleic acid), 9-eicosenoic acid (gadoleic acid), 13-docosenoic acid (erucic acid), 15-tetracosenoic acid (nervonic acid), 9,12-octadecadienoic acid (linoleic acid), and linolenic acid (9,12,15-octadecatrienoic acid).

5. Process according to claim 4, wherein the unsaturated carboxylic acid is a monounsaturated carboxylic acid.

6. Process according to claim 1, wherein the catalyst of step a) is used in a homogeneous or heterogeneous phase, optionally in a supported or nanostructured form, and belongs to the group of transition elements and acids, salts and complexes thereof 7. Process according to claim 6, wherein the catalyst of step a) is selected from the group of tungsten and molybdenum derivatives or mixtures thereof, said catalyst being present in a quantity between 0.03% and 3% by moles with respect to the total moles of unsaturations.

8. Process according to claim 1, wherein the catalyst of step b) is used in a homogeneous or heterogeneous phase, optionally in a supported or nanostructured form, and belongs to the group of transition elements and acids, salts and complexes thereof

9. Process according to claim 8, wherein the catalyst of step b) is selected from the group of the derivatives of cobalt and manganese, including acetates, chlorides, sulphates, bromides and nitrates, said catalyst being present in a quantity between 0.05% and 3% by moles with respect to the diol.

10. Process according to claim 1, wherein the oxidizing compound of step (a) is hydrogen peroxide present in aqueous solution in concentrations between 30 and 80%, the oxidizing compound of step (b) being air.

11. Process according to claim 1, wherein step (a) is carried out at a pressure equal to or slightly lower than the atmospheric pressure, while step b) is carried out at a pressure higher than the atmospheric pressure.

12. Process according to claim 1, wherein the reaction temperature of step a) and of step b) is comprised between 45 and 95° C.

13. Process according to claim 1, wherein step c) is carried out by distillation.

14. Process according to claim 1, wherein step d) is carried out by using only water, acid ion exchange resins or lipases.

15. Process according to claim 1, wherein step d) is performed with water at 260-300° C. in a plug flow tubular reactor.

16. Process according to claim 15, wherein the saturated carboxylic acid having more than one acid function is purified by thin layer distillation, followed by distillation and water extraction.

17. Process according to claim 14, wherein the saturated carboxylic acid having more than one acid function is purified by thin layer distillation, followed by distillation and water extraction.

18. Process according to claim 5, wherein the monounsaturated carboxylic acid is 9-octadecenoic acid (oleic acid).

19. Process according to claim 5, wherein the monounsaturated carboxylic acid is 13-docosenoic acid (erucic acid).

20. Process according to claim 13, wherein the distillation is by thin layer distillation.

* * * * *